United States Patent [19]

Cuffiani et al.

[11] 4,390,454
[45] Jun. 28, 1983

[54] CATALYST COMPONENTS FOR POLYMERIZING OLEFINS

[75] Inventors: Illaro Cuffiani; Paolo Galli; Umberto Zucchini, all of Ferrara, Italy

[73] Assignee: Montedison S.p.A., Milan, Italy

[21] Appl. No.: 285,961

[22] Filed: Jul. 23, 1981

[30] Foreign Application Priority Data

Jul. 24, 1980 [IT] Italy ................. 23656 A/80

[51] Int. Cl.$^3$ ................................. C08F 4/64
[52] U.S. Cl. ........................... 252/429 B; 252/429 C; 526/114; 526/116; 526/119; 526/127; 526/128
[58] Field of Search ................... 252/429 B, 429 C

[56] References Cited

U.S. PATENT DOCUMENTS 3,454,547 7/1969 Delbouille et al. ......... 252/429 C X
4,190,555 2/1980 Takamura et al. ......... 252/429 C X
4,199,475 4/1980 Welch et al. ................ 252/429 C
4,218,339 8/1980 Zucchini et al. ............ 252/429 B

FOREIGN PATENT DOCUMENTS 1401708 7/1975 United Kingdom .

Primary Examiner—Patrick Garvin

[57] ABSTRACT

There are disclosed components of catalysts for polymerizing ethylene and mixtures of ethylene with alpha-olefins comprising the reaction product of (A) a magnesium compound, such as Mg-chloride, Mg-alcoholate or a Grignard compound, with (B) a titanium, vanadium or zirconium compound having at least two metal-oxygen bonds, such as a tetra-alcoholate, and with (C) a halogenated compound of metals of B, such as Ti tetrachloride.

According to an aspect of the invention, the reaction product (A)+(B), before being reacted with (C), is treated with a silicum compound having a halogenating and/or reducing action.

The catalysts according to the invention are suitable for obtaining ethylene polymers having a broad distribution of molecular weights.

8 Claims, No Drawings

CATALYST COMPONENTS FOR POLYMERIZING OLEFINS

BACKGROUND OF THE INVENTION

Catalyst systems for the polymerization of ethylene or mixtures thereof with higher alpha-olefins are known and described in several patents, and the polymers obtained show a rather narrow distribution of molecular weights. Said polymers are suitable for injection molding and for other applications but are not satisfactory for the manufacture of articles by extrusion or blowing. In fact, it is known that, due to the narrow distribution of the molecular weights, the polymers are subject to breaking phenomena of the molten mass during the forming process and, furthermore, the articles prepared according to the above-mentioned techniques present knurlings.

In practice, the value of the ratio MI N/MI E is assumed as a measure of the breadth of the molecular weight distribution, MI N and MI E being the melt indexes of the polymer measured at 190° C. with a weight of 10.00 Kg and of 2.16 Kg respectively (ASTM D 1238). Polymers with about the same value of melt index MI E have broader molecular weight distribution if the value of the MI N is higher.

Different methods can be used in order to obtain polymers with a rather broad molecular weight distribution. The simplest consists in suitably modifying the catalyst system, but such method often involves several drawbacks, such as, for example, an excessive decrease of the catalyst activity and/or difficulties in the regulation of the molecular weight of polymers.

THE PRESENT INVENTION

An object of this invention is to provide new catalyst-forming components which yield, when mixed with a metal-alkyl of a Group I-III metal, catalysts which polymerize ethylene and mixtures of ethylene with up to 20% by weight, referred to the total weight, of alpha-olefins $CH_2=CHR$ in which R is a $C_1-C_6$ alkyl radical, to polymers or copolymers having a broad distribution of molecular weights.

Another object is to provide catalyst-forming components which yield final catalysts that polymerize ethylene and mixtures thereof with said alpha-olefins to polymers or copolymers which are useful for manufacturing shaped articles by extrusion or blowing without the aforesaid disadvantages of the polymers or copolymers showing a narrow weight distribution.

These and other objects are achieved by the present invention, in accordance with which we have found, surprisingly, new components of catalysts for polymerizing ethylene which have high activity and permit the obtention of ethylene polymers having a broad distribution of molecular weights without presenting the disadvantages mentioned hereinabove. Such catalyst components are characterized by a high titanium, V or Zr content and by a low chlorine content.

The catalyst components of the present invention comprise the product obtained by reacting:

(A) a magnesium compound selected from
  (1) compounds of formula: $X_nMg(OR)_{2-n}$ wherein X is Cl or Br, a group —OH, an alkyl, aryl or a cycloalkyl having 1 to 20 carbon atoms; R is an alkyl, an aryl or a cycloalkyl having 1 to 20 carbon atoms, or a group —COR' in which R' is a hydrocarbon radical equal to R; $0 \leq n \leq 2$;
  (2) compounds of formula: RMgX wherein X is Cl or Br and R is an alkyl, an aryl or a cycloalkyl having 1 to 20 carbon atoms;
  (3) MgO, $Mg(OH)_2$, XMgOH, in which X is Cl or Br; and (B) a compound of Ti, V or Zr having at least two metal-oxygen bonds of the type Ti-OR or Zr-OR in which R is an alkyl, an aryl or a cycloalkyl having 1 to 20 carbon atoms or the group

with (C) a halogenated compound of a transition metal of groups IV, V, VI of the Periodic System having formula $MO_mX_n$ in which M is a transition metal, for example Ti, V or Zr, X is Cl or Br, $m \geq 0$, $n > 0$, $2m+n$ is equal to the valence of metal M.

Examples of compounds (A) are: $MgCl_2$ which is the preferred compound, $MgBr_2$, the magnesium mono- and dialcoholates, as $Mg(OC_2H_5)_2$, $Mg(O-n-C_4H_9)_2$, $C_2H_5OMgCl$, $n-C_4H_9MgCl$, magnesium carboxylates such as $(CH_2COO)_2Mg$, Grignard compounds such as $C_2H_5MgCl$, $n-C_4H_9MgCl$, $n-C_4H_9MgBr$, and ClMgOH.

Examples of compounds (B) are $Ti(OC_2H_5)_4$, $Ti(O-n-C_4H_9)_4$, $Ti(O-i-C_3H_7)_4$, $Ti(OC_6H_5)_4$, $V(O-i-C_3H_7)_4$, $VO(O-i-C_3H_7)_3$, titanium triacetylacetonate, $Ti(OCH_3)_2(OC_2H_5)_2$, $Zr(O-n-C_4H_9)_4$. It is possible also to use halogen-alcoholates such as $ClTi(O-n-C_4H_9)_3$.

Examples of compounds (C) are: $TiCl_4$, $TiBr_4$, $VCl_3$, $VCl_4$, $VOCl_3$, $ZrCl_4$, the preferred compound being $TiCl_4$.

The metal of halogenated compound (C) may be the same as or different from that of compound (B).

Compounds (A) and (B) are reacted in an atomic ratio transition metal/Mg ranging from 0.02 to 20, preferably from 0.1 to 3. The reaction is carried out in an aliphatic, a cycloaliphatic or an aromatic hydrocarbon diluent or in the absence of diluent, at a temperature ranging from 20° C. to 200° C. to obtain a homogeneous product which is then reacted with halogenated compound (C).

Compound (C) is employed in such amounts as to have a (C)/(B) molar ratio ranging from 2 to 20, preferably from 4 to 10.

The reaction between the reaction product (A) with (B) and the compound (C) is generally carried out at temperatures ranging from 10° C. to 200° C., preferably from 50° C. to 150° C.

Compound (C) may be employed as such or diluted in a solvent like the ones indicated for the reaction between (A) and (B).

According to one embodiment of the invention, prior to the treatment with compound (C), the reaction product of (A) and (B) is reacted with a silicium compound capable of a halogenating action or a reducing action or a halogenating and simultaneous reducing action on compound (B). Silicium halides, preferably silicium chlorides, or Si-hydrides and compounds containing atoms of halogen and hydrogen directly bound to a silicium atom are suitable for this purpose. Examples of such compounds are: $SiCl_4$, $Si_4Cl_{10}$, $Si_2OCl_6$, $C_2H_5SiCl_3$, $Si(OC_2H_5)Cl_3$, $Si_3H_8$, polysilanes $(SiH)_x$ wherein x has a value of at least 2, $(C_6H_5)_3SiH$, (C₂H₅O)₃SiH, polyhydrosiloxanes containing the monomeric unit

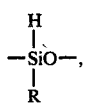

in which R is H, a halogen, an alkyl with 1 to 10 carbon atoms, an aryl, an alkoxyl, an aryloxyl or a carboxyl, and having a polymerization degree comprised between 2 and 1,000, preferably between 3 and 100. Examples of such polyhydrosiloxanes are: (CH₃HSiO)₄, H₃Si-O-SiH₂-OSiH₃ and the polymethylhydrosiloxane (PMHS) of formula (CH₃)₃SiO[(CH₂)HSiO]$_n$Si(CH₃)₃, wherein n has a value of about 35.

Examples of silicium compounds capable of exerting simultaneously a halogenating and a reducing action are the following: SiHCl₃, SiH₂Cl₂, SiH₃Cl, CH₃SiCl₂H and C₂H₅SiClH₂.

Mixtures of two silicium compounds, one having a halogenating action only and the other a reducing action only can be used.

The silicium compounds exerting a halogenating action are capable of substituting at least one group —OR of compound (B) with a halogen atom.

The silicium compound is employed in such an amount as to have from 0.5 to 100, preferably from 1 to 30, gram atoms of halogen per gram atom of Ti, V or Zr and from 0.1 to 100, preferably from 0.5 to 20, gram equivalent of reducing agent per gram atom of Ti, V or Zr.

The reaction with the silicium compound is carried out at a temperature ranging from 20° C. to 200° C. and, also in this case, the use of a hydrocarbon diluent is optional.

Catalyst components prepared by reacting compound (A) with compound (B) and by successively reacting the resulting product with one or more silicium compounds having a halogenating and a reducing action are described in U.S. Pat. No. 4,218,339, but the corresponding catalysts provide ethylene polymers having a narrow molecular weight distribution.

In case of treatment with the silicium compound, such treatment can be carried out after the reaction of product (A) and (B) with compound (C). Practically it is preferred to treat the reaction product of (A) and (B) with a silicium compound and then to react the resulting product with compound (C).

By suitably choosing the catalyst component preparation conditions it is possible to affect the distribution of the molecular weights of the polymers or copolymers.

The catalyst components of the present invention are employed in combination with a cocatalyst consisting of a metal-alkyl of a metal of Groups I, II or III of the Periodic System, preferably an Al-trialkyl.

The polymerization of ethylene and the mixtures thereof with alpha-olefins is carried out according to the known methods in liquid phase in presence of an inert hydrocarbon diluent or in gas phase.

The polymerization temperature is generally comprised between 40° and 120° C. Higher temperatures ranging for example between 150° and 300° C. can be used.

In the following examples, which are given to illustrate this invention in more detail without, however, being a limitation thereof, the polymerization of ethylene was carried out as described in Example 1, i.e., in 1,000 cc of n-hexane containing 1.5 g of Al(i-C₄H₉)₃, at 75° C. and at a pressure of 14 atm., for 4 hours; the partial pressures of hydrogen (for the regulation of molecular weight) and of ethylene are specified in the examples.

Examples 1 to 4 (Table I) refer to catalyst components prepared by directly treating the reaction product of MgCl₂ and Ti alcoholate with TiCl₄.

Examples A, B, C, D (Table II) are comparative examples that show that catalyst components obtained by reacting the reaction products of MgCl₂+Ti alcoholate with silicium compounds provide polymers having a narrow molecular weight distribution (the MI N/MI E ratio is not higher than 8.5).

Furthermore, the catalyst components prepared in examples A and B are employed in Examples 5 to 12.

Examples 5 to 14 (Table III) relate to catalyst components prepared according to the alternative method which uses silicium compounds.

EXAMPLE 1

2.4 g of anhydrous MgCl₂ were dissolved in 17 g of Ti(O-n-C₄H₉)₄ by heating at 140° C. under stirring for 3 hours. The solution obtained was diluted with 45 cc of ISOPAR G and 95 g of TiCl₄ were added thereto in 90 minutes; the mixture was then heated at 135° C. under stirring for 2 hours. At the end, the resulting solid product was isolated by filtration at 60° C. and repeatedly washed with 50 cc of anhydrous n-hexane at room temperature until disappearance of the chlorine ions from the solvent. After drying under vacuum at 40° C. for 3 hours, a catalyst component containing 22.3% of Ti was obtained.

For the ethylene polymerization test, 1,000 cc of anhydrous n-hexane, 1.5 g of Al(i-C₄H₉)₃ as cocatalyst and 0.0082 g of the above-mentioned catalyst component were introduced in the order stated into a stainless steel 2.5-liter autoclave equipped with a stirrer. The autoclave was heated at 75° C. and 3 hydrogen atmospheres with 10 ethylene atmospheres were introduced feeding continuously ethylene to maintain the total pressure at 14 atmospheres. After 4 hours, the polymerization was interrupted, the polymer was isolated by filtration and then was dried. The results of the polymerization test are reported in Table I.

EXAMPLE 2

4.75 g of anhydrous MgCl₂ and 23.0 g of Ti(OC₂H₅)₄ were added to 90 cc of ISOPAR G, whereupon the mixture was heated at 100° C. under stirring for 3 hours. 95 g of TiCl₄ were added in 90 minutes to the resulting solution which was heated at 135° C. under stirring for 2 hours. By filtration at 60° C. a solid product was isolated which was repeatedly washed at room temperature with 50 cc of anhydrous n-hexane until thorough removal of free TiCl₄ from the product. The catalyst component so prepared, after drying under vacuum at 40° C. for 3 hours, contained 29.45% of Ti.

The result of the ethylene polymerization test (H₂ pressure: 3 atm., C₂H₄ pressure: 10 atm.) is recorded in Table I.

EXAMPLE 3

2.4 g of anhydrous MgCl₂ were dissolved in 17 g of Ti(O-n-C₄H₉)₄ by heating at 140° C. under stirring for 3 hours. The resulting solution was diluted with 45 cc of n-heptane, 95 g of TiCl₄ were added thereto in 90 minutes and the mixture was then heated at 98° C. under stirring for 2 hours. The solid product was isolated by filtration, repeatedly washed at room temperature with 50 cc of n-heptane and then dried under vacuum at 40° C. for 3 hours. A catalyst component containing 22.8% of Ti was obtained.

The result of the polymerization test ($H_2$ pressure: 4 atm., $C_2H_4$ pressure: 9 atm.) is recorded in Table I.

EXAMPLE 4

2.4 g of anhydrous $MgCl_2$ were dissolved in 17 g of Ti$(O-n-C_4H_9)_4$ by heating at 140° C. under stirring for 3 hours. The solution so obtained was added, after dilution with 45 cc of anhydrous n-hexane, with 19 g of $TiCl_4$ in 90 minutes at room temperature, and the resulting suspension was then heated at 60° C. under stirring for 2 hours. The solid product was separated by filtration at 60° C. and was repeatedly washed with 50 cc of anhydrous n-hexane at room temperature until the chlorine ions disappeared.

After drying under vacuum at 40° C. for 3 hours, a catalyst component containing 8.6% of Ti was obtained.

The result of the polymerization test ($H_2$ pressure: 3 atm., $C_2H_4$ pressure: 10 atm.) is recorded in Table I.

EXAMPLE B

A catalytic component was prepared as in Example A by employing:

- 2.2 g of anhydrous $MgCl_2$
- 17 g of Ti$(O-n-C_4H_9)_4$
- 34 cc of anhydrous n-heptane
- 38 g of $SiCl_4$
- 17 g of PMHS.

7 g of a solid catalytic component containing 8% of Ti were obtained.

The result of the ethylene polymerization test ($H_2$ pressure: 5 atm., $C_2H_4$ pressure: 8 atm.) is recorded in Table II.

EXAMPLE C 2.4 g of anhydrous $MgCl_2$ were added to 17 g of Ti$(O-n-C_4H_9)_4$ and the mixture was heated at 140° C. for 3 hours, so obtaining a solution which was diluted with 45 cc of n-hexane. 17 g of $SiCl_4$ were added at room temperature to such solution and successively, under stirring, the mixture was heated at 60° C. for 2 hours. The resulting solid product was separated by filtration at 60° C., it was repeatedly washed with portions of 50 cc of anhydrous n-hexane at room tempera-

TABLE I

| | SILICIUM-FREE CATALYTIC COMPONENTS | | | | | | | | |
|---|---|---|---|---|---|---|---|---|---|
| | Direct treatment of reaction product (A) + (B) with $TiCl_4$ | | | | Polymerization | | | Polyethylene | |
| Example No. | Diluent cc | $TiCl_4$ g | Temperature °C. | Time hours | % of Ti in catalytic component | Catalytic component g | Polymer g | Yield g polymer/ g/Ti | MI E g/10 min. | MI N/ MI E |
| 1* | 45 (Isopar G)*** | 95 | 135 | 2 | 22.3 | 0.0082 | 291 | 160,000 | 0.09 | 12.0 |
| 2** | 90 (Isopar G) | 95 | 135 | 2 | 29.45 | 0.0080 | 269 | 114,000 | 0.075 | 13.3 |
| 3* | 45 (n-heptane) | 95 | 98 | 2 | 22.8 | 0.0095 | 342 | 158,000 | 0.15 | 10.5 |
| 4* | 45 (n-hexane) | 19 | 60 | 2 | 8.6 | 0.0080 | 420 | 609,000 | 0.23 | 9.6 |

*(A) + (B): reaction product of 2.4 g of $MgCl_2$ with 17 g of Ti(O—n-$C_4H_9$)$_4$.
**(A) + (B): reaction product of 4.75 g of $MgCl_2$ with 23.0 g of Ti(O$C_2H_5$)$_4$.
***Mixture of isoparaffinic hydrocarbons boiling in the temperature range of from 158° to 172.5° C.

EXAMPLE A

A catalytic component of the type (A)+(B)-+silicium compound, like those described in U.S. Pat. No. 4,218,339, was prepared from the following reagents:

- 2.15 g of anhydrous $MgCl_2$
- 16.6 g of Ti$(O-n-C_4H_9)_4$
- 32 cc of anhydrous n-heptane
- 12.5 g of $SiCl_4$
- 8.9 g of PMHS (polymethylhydrosilozane, produced and sold by Farbenfabriken Bayer under the commercial name BAYSILON MH 15).

By operating as indicated in the description of said patent it was possible to obtain 10 g of a solid catalytic component containing 15.5% of Ti.

The result of the ethylene polymerization test ($H_2$ pressure: 5 atm., $C_2H_4$ pressure: 8 atm.) is recorded in Table II.

ture until the disappearance of the chlorine ions from the solvent and then it was dried under vacuum at 40° C. for 3 hours. The catalytic component so obtained contained 2.5% of Ti.

The result of the polymerization test ($H_2$ pressure: 3 atm., $C_2H_4$ pressure: 10 atm.) is recorded in Table II.

EXAMPLE D

A solution of $MgCl_2$ in Ti$(O-n-C_4H_9)_4$, diluted with n-hexane and prepared as described in Example C, was additioned with 17 g of polymethylhydrosiloxane at 45° C., under stirring, in 90 minutes. Subsequently, also in 90 minutes, 85 g of $SiCl_4$ were added. The suspension so obtained was heated at 60° C. under stirring for 2 hours. By filtering such suspension at 60° C., a catalytic component was isolated, which was washed and dried as described in Example C; its Ti content was 4.5%.

The result of the polymerization test ($H_2$ pressure: 3 atm., $C_2H_4$ pressure: 10 atm.) is recorded in Table II.

TABLE II

COMPARATIVE EXAMPLES

| Example No. | % of Ti in the catalyst component | Polymerization Catalyst component g | Polymer g | Yield g polymer/g Ti | Polyethylene MI E g/10 min. | MI N/ MI E |
|---|---|---|---|---|---|---|
| A | 15.5 | 0.0100 | 279 | 180,000 | 0.9 | 8.0 |
| B | 8.0 | 0.0056 | 148 | 330,000 | 0.85 | 8.5 |
| C | 2.5 | 0.0097 | 225 | 930,000 | 0.4 | 8.5 |
| D | 4.5 | 0.0088 | 226 | 571,000 | 0.28 | 8.4 |

EXAMPLE 5

10 g of a catalyst component prepared according to Example A were suspended in 40 cc of anhydrous n-heptane containing 42 g of $TiCl_4$. The mixture was heated at 98° C. under stirring for 2 hours, then allowed to cool to 60° C. and the liquid phase was removed by syphoning. The solid residue was repeatedly washed at room temperature with portions of 50 cc of anhydrous n-hexane until disappearance of the chlorine ions from the solvent, and finally it was dried under vacuum at 40° C. for 3 hours.

The catalytic component so obtained contained 23.0% of Ti.

The result of the ethylene polymerization test ($H_2$ pressure: 5 atm., $C_2H_4$ pressure: 8 atm.) is recorded in Table III.

EXAMPLES 6, 7, 8, 9 and 10

Always starting from 10 g of a catalyst component prepared as in Example A, other components were prepared as described in Example 5, but with the differences indicated in Table III.

The results of the polymerization tests ($H_2$ pressure: 5 atm., $C_2H_4$ pressure: 8 atm.) are recorded in the same Table.

EXAMPLE 11

10 g of a catalyst component prepared as in Example B were reacted with the amount of $TiCl_4$ and under the conditions as indicated in Table III, to obtain a catalyst component containing 12.05% of Ti which was used for carrying out the polymerization of ethylene ($H_2$ pressure: 5 atm., $C_2H_4$ pressure: 8 atm.).

The result of such test is recorded in Table III.

EXAMPLE 12

10 g of a catalyst component prepared as in Example A were suspended in 40 cc of anhydrous n-hexane at room temperature and the resulting suspension was additioned, in 30 minutes and under stirring, with 55 g of $VOCl_3$. The mixture was heated at 60° C. under stirring for 1 hour. At 60° C., after decantation of the solid product, the liquid phase was removed by syphoning. The solid product was repeatedly washed at room temperature with 50 cc of anhydrous n-hexane and then dried under vacuum at 40° C. for 3 hours. A catalyst component was obtained which contained 4.95% of Ti and 21.0% of V.

The result of the polymerization test ($H_2$ pressure: 5 atm., $C_2H_4$ pressure: 8 atm.) is recorded in Table III.

EXAMPLE 13

2.4 g of anhydrous $MgCl_2$ were dissolved in 17 g of $Ti(O-n-C_4H_9)_4$ by heating at 140° C. under stirring for 3 hours. The resulting solution was diluted with 45 cc of ISOPAR G (a mixture of isoparaffinic hydrocarbons produced by Esso Chemical Co., boiling in the temperature range of from 158° to 172.5° C.) and maintaining said solution at 45° C. and under stirring, 17 g of polymethylhydrosiloxane were added thereto in 90 minutes. The resulting suspension was additioned, always at 45° C., with 95 g of $TiCl_4$ in 90 minutes, whereupon it was reacted at 135° C. under stirring for 2 hours.

After cooling to 60° C., the solid catalytic component so formed was isolated by filtration and it was repeatedly washed, at room temperature, with 50 cc of n-hexane each time. After drying under vacuum at 40° C. for 3 hours, said catalyst component contained 25.75% of Ti.

The result of the polymerization test ($H_2$ pressure: 7 atm., $C_2H_4$ pressure: 6 atm.) is recorded in Table III.

EXAMPLE 14

The solution of $MgCl_2$ in $Ti(O-n-C_4H_9)_4$ diluted with n-hexane and prepared as described in Example C was additioned, in 90 minutes, at 45° C. and under stirring, with 17 g of polymethylhydrosiloxane and successively, also in 90 minutes, with 95 g of $TiCl_4$. The resulting suspension was then heated at 60° C. with continuous stirring at that temperature for 2 hours. By filtering the suspension at 60° C. a solid catalyst component was isolated which was repeatedly washed with 50 cc of n-hexane each time until the chlorine ions disappeared from the solvent. Finally, it was dried under vacuum at 40° C. for 3 hours. The catalyst component so prepared contained 25.45% of Ti.

The result of the polymerization test ($H_2$ pressure: 5 atm., $C_2H_4$ pressure: 8 atm.) is recorded in Table III.

TABLE III

SILICIUM-CONTAINING CATALYST COMPONENTS

| Example No. | Treatment of intermediate catalytic components (containing silicium) Diluent cc | $TiCl_4$ g | Temperature °C. | Time hours | % of Ti in catalytic component | Polymerization Catalytic component g | Polymer g | Yield g polymer/ g/Ti | Polyethylene MI E g/10 min. | MI N/ MI E |
|---|---|---|---|---|---|---|---|---|---|---|
| 5* | 40 (n-heptane) | 42 | 98 | 2 | 23.0 | 0.0087 | 200 | 100,000 | 0.21 | 11.5 |
| 6* | 40 (n-hep- | 84 | 98 | 2 | 20.2 | 0.0086 | 234 | 135,000 | 0.39 | 10.8 |

TABLE III-continued

SILICIUM-CONTAINING CATALYST COMPONENTS

| Example No. | Treatment of intermediate catalytic components (containing silicium) | | | | % of Ti in catalytic component | Polymerization | | Yield g polymer/ g/Ti | Polyethylene | |
|---|---|---|---|---|---|---|---|---|---|---|
| | Diluent cc | TiCl$_4$ g | Temperature °C. | Time hours | | Catalytic component g | Polymer g | | MI E g/10 min. | MI N/ MI E |
| 7* | — (tane) | 84 | 60 | 2 | 18.8 | 0.0063 | 248 | 210,000 | 0.61 | 10.7 |
| 8* | — | 84 | 100 | 2 | 21.35 | 0.009 | 160 | 83,000 | 0.25 | 12.5 |
| 9* | — | 84 | 136 | 2 | 23.15 | 0.010 | 215 | 93,000 | 0.14 | 11.4 |
| 10* | — | 84 | 136 | 5 | 21.45 | 0.011 | 197 | 84,000 | 0.09 | 12.0 |
| 11** | — | 130 | 136 | 2 | 12.05 | 0.006 | 188 | 261,000 | 0.27 | 10.7 |
| 12* | 40 (n-hexane) | 55 VOCl$_3$ | 68 | 1 | 4.95  21.0 Ti    V | 0.021 | 20 | 19,000 | 0.065 | 18.8 |
| 13 | 45 (Isopar G) | 95 | 135 | 2 | 25.75 | 0.0132 | 200 | 59,000 | 0.12 | 14.6 |
| 14 | 45 (n-hexane) | 95 | 60 | 2 | 25.45 | 0.0115 | 235 | 80,000 | 0.20 | 10.6 |

*10 g of the catalyst component of Example A were employed.
**10 g of the catalyst component of Example B were employed.

What is claimed is:

1. Components of catalysts for the polymerization of olefins, comprising the product which is obtained by reacting the reaction product between:
   (A) a magnesium compound selected from
       (1) compounds of formula $X_nMg(OR)_{2-n}$ wherein X is Cl or Br, a group —OH, an alkyl, an aryl or a cycloalkyl having 1 to 20 carbon atoms; R is an alkyl, an aryl or a cycloalkyl having 1 to 20 carbon atoms, or a group —COR′ in which R′ is a hydrocarbon radical as specified for R; $0 \leq n \leq 2$;
       (2) MgO, Mg(OH)$_2$, XMgOH, in which X is Cl or Br; and
   (B) a compound of titanium, vanadium or zirconium having at least two metal-oxygen bonds of the type Ti-OR, V-OR, or Zr-OR, in which R is an alkyl, an aryl or a cycloalkyl having 1 to 20 carbon atoms or the group

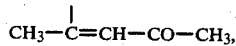

with
   (C) a halogenated compound of a transition metal of Groups IV, V, VI of the Periodic System of formula $MO_mX_n$ in which M is a transition metal, X is Cl or Br, $m \geq 0$, $n > 0$, $2m+n$ being equal to the valence of metal M.

2. Catalyst components according to claim 1, comprising the product obtained by reacting the product of the reaction between MgCl$_2$ and Ti(O-n-C$_4$H$_9$)$_4$ with TiCl$_4$.

3. Catalyst components according to claim 1, comprising the product obtained by reaction of TiCl$_4$ with the product of the reaction between MgCl$_2$ and Ti(OC$_2$H$_5$)$_4$.

4. Catalyst components according to claim 1, consisting of the product obtained by reacting the product of the reaction between compounds (A) and (B) with a silicon compound having a halogenating and/or reducing action and then with compound (C).

5. Catalyst components according to claim 4, consisting of the product which is obtained by reacting the product of the reaction between MgCl$_2$ and Ti(O-n-C$_4$H$_9$)$_4$ with a mixture of SiCl$_4$ and polymethylhydrosiloxane and then with TiCl$_4$.

6. Catalyst components according to claim 4, consisting of the product which is obtained by reacting the product of the reaction between MgCl$_2$ and Ti(O-n-C$_4$H$_9$)$_4$ with a mixture of SiCl$_4$ and polymethylhydrosiloxane and then with VOCl$_3$.

7. Catalyst components according to claim 4, consisting of the product which is obtained by reacting the product of the reaction between MgCl$_2$ and Ti(O-n-C$_4$H$_9$)$_4$ with polymethylhydrosiloxane and then with TiCl$_4$.

8. Catalysts for polymerizing ethylene, consisting of a combination of a catalyst component according to any one of claims 1 to 3 with an aluminum alkyl compound.

* * * * *